US012702341B2

(12) United States Patent
El-Khamy et al.

(10) Patent No.: US 12,702,341 B2
(45) Date of Patent: Aug. 11, 2026

(54) SYSTEM AND METHOD FOR CONTINUOUS ATRIAL FIBRILLATION DETECTION VIA PPG TO ECG SIGNAL TRANSLATION

(71) Applicant: Samsung Electronics Co., Ltd., Gyeonggi-do (KR)

(72) Inventors: Mostafa El-Khamy, San Diego, CA (US); Khuong Vo, Irvine, CA (US); Yoojin Choi, San Diego, CA (US)

(73) Assignee: Samsung Electronics Co., Ltd (KR)

(*) Notice: Subject to any disclaimer, the term of this patent is extended or adjusted under 35 U.S.C. 154(b) by 279 days.

(21) Appl. No.: 18/458,268

(22) Filed: Aug. 30, 2023

(65) Prior Publication Data

US 2024/0122519 A1 Apr. 18, 2024

Related U.S. Application Data

(60) Provisional application No. 63/458,303, filed on Apr. 10, 2023, provisional application No. 63/411,914, filed on Sep. 30, 2022.

(51) Int. Cl.

| | |
|---|---|
| ***A61B 5/327*** | (2021.01) |
| ***A61B 5/024*** | (2006.01) |
| ***A61B 5/352*** | (2021.01) |
| ***A61B 5/361*** | (2021.01) |

(52) U.S. Cl.

CPC .......... *A61B 5/327* (2021.01); *A61B 5/02416* (2013.01); *A61B 5/352* (2021.01); *A61B 5/361* (2021.01)

(58) Field of Classification Search

None

See application file for complete search history.

(56) References Cited

U.S. PATENT DOCUMENTS

| | | | | |
|---|---|---|---|---|
| 11,154,254 | B2 | 10/2021 | Najarian et al. | |
| 11,399,775 | B2 | 8/2022 | Stephens | |
| 2020/0184338 | A1* | 6/2020 | Volkovs | G06N 3/0455 |
| 2021/0052175 | A1 | 2/2021 | Stephens et al. | |
| 2021/0315470 | A1* | 10/2021 | Wu | A61B 5/327 |
| 2022/0175300 | A1 | 6/2022 | Nathan et al. | |
| 2023/0078489 | A1 | 3/2023 | Cho et al. | |

FOREIGN PATENT DOCUMENTS

| | | |
|---|---|---|
| EP | 3 708 071 | 3/2019 |

OTHER PUBLICATIONS

Banerjee, Rohan, PhotoECG: Photoplethysmography to estimate ECG parameters, In 2014 IEEE International Conference on Acoustics, Speech and Signal Processing (ICASSP), 2014, 5 pgs.

(Continued)

*Primary Examiner* — Ankit D Tejani

(74) *Attorney, Agent, or Firm* — The Farrell Law Firm, P.C.

(57) ABSTRACT

A system and a method are disclosed for AFib detection using ECG signals generated from monitored PPG signals. A method includes receiving PPG signals of a user measured by a PPG sensor; translating the measured PPG signals into ECG signals using a dynamic model; analyzing the translated ECG signals using an AFib detection model, which is trained on measured ECG signals for AFib detection; and providing the analyzed AFib detection results to the user.

20 Claims, 12 Drawing Sheets

(56) References Cited

OTHER PUBLICATIONS

Qiang Zhu et al., "ECG reconstruction via PPG: A Pilot Study", In 2019 IEEE EMBS International Conference on Biomedical & Health Informatics (BHI), 2019, 4 pgs.
Xin Tian et al., "Cross-domain Joint Dictionary Learning for ECG Reconstruction from PPG", In ICASSP, International Conference on Acoustics, Speech and Signal Processing, 2020, 14 pgs.
Khuong Vo et al., P2E-WGAN: ECG waveform synthesis from PPG with Conditional Wasserstein Generative adversarial networks, In Proceedings of the 36th Annual ACM Symposium on Applied Computing, 2021, 1030-1036 pgs.
Pritam Sarkar et al., Cardio/GAN: "Attentive Generative Adversarial Network with Dual Discriminators for Synthesis of ECG from PPG", In Proceedings of the AAAI Conference on Artificial Intelligence, vol. 35, 2021, 488-496 pgs.
Hong-Yu Chiu et al., "Reconstructing QRS Complex from PPG by Transformed Attentional Neural Networks", IEEE Sensors, 2020, 10 pgs.
Tao-Yi Lee et al., "STINT: Selective Transmission for Low-Energy Physiological Monitoring", In Proceedings of the ACM/IEEE International Symposium on Low Power Electronics and Design, 2020, 6 pgs.
Moraes et al., "Advances in Photopletysmography Signal Analysis for Biomedical Applications", 2018, 26 pgs.
Dinakarrao et al, "Computer-Aided Arrhythmia Diagnosis with Bio-signal Processing: A Survey of Trends and Techniques", ACM Computing Surveys, vol. 9, No. 4, Mar. 2019, 36 pgs.
Shenda Hong et al., "MINA: Multilevel Knowledge-guided Attention for Modeling Electrocardiogramals", International Joint Conference on Artificial Intelligence, (IJCAI), 2019, 9 pgs.
Paul Kligfield et al., "Recommendations for the Standardization and Interpretation of the Electrocardiogram: Part 1: The Electrocardiogram and It's Technology", Endorsed by the International Society for Computerized Electrocardiology, 2007, 19 pgs.
Le, T. et al., "Electrocardiogram: Acquisition and Analysis for Biological Investigations and Health Monitoring", In Interfacing Bioelectronics and Biomedical Sensing, Springer, 2020, 26 pgs.
Allen, J. "Photoplethysmography and it's Application in Clinical Physiological Measurement", Physiological Measurement 28, 2007, 39 pgs.
Mayo Clinic Staff, Sudden Death in Young People: Heart Problems often blamed (retrieved on Sep. 2020), https://www.mayoclinic.org/diseases-conditions/sudden-cardiac-arrest/indepth/sudden-death/art-20047571, 4 pages.
Anna Rosiek et al., "The Risk Factors and Prevention of Cardiovascular Disease: The Importance of Electrocardiogram in the Diagnosis and Treatment of Acute Coronary Syndrome, Therapeutics and Clinical Risk Managment," 2016, 7 pgs.
Ivan Olier et al., "How Machine Learning in Impacting Research in Atrial Fibrillation: Implications for Risk Prediction and Future Managment", Cardiovascular Research, 2021, 18 pgs.
Andrew Reisner, Utility of the Photoplethysmogram in Circulatory Monitoring, Anesthesiology, The American Society of Anesthesiologists, 2008, 9 pgs.
Diederik P. Kingma et al., "Auto-Encoding Variational Bayes", arXiv:1312.6114v3, Dec. 24, 2013, 9 pages.
Rahul G. Krishnan et al., "Deep Kalman Filters", arXiiv Preprint arXiv:1511.05121, 2015, 17 pgs.
Krishnan et al., "Structured Inference Networks for Nonlinear State Space Models", In Proceedings of the AAAI Conference on Artificial Intelligence, 2017, 13 pgs.
Dzmitry Bahdanau et al., "Neural Machine Translation by Jointly Learning to Align and Translate", arXiv preprint arXiv:1409.0473, 2014, 15 pgs.
Dan Geiger et al., "Identifying Independence in Bayesian Networks", 1990, 28 pgs.
Junyoung Chung et al., "Empirical Evaluation of Gated Recurrent Neural Networks on Sequence Modeling", arXiv preprint arXiv:1412.3555, 2014, 9 pgs.
Diederik P. Kingma et al., "ADAM: A Method for Stochastic Optimization", arXiv preprint arXiv: 1412.6980v9, 2015, 15 pgs.
Benjamin Moody et al., "Mimic-Ill Waveform Database Matched Subset", PhysioNet Version 1.0, Apr. 7, 2020, 5 pgs.
Alistar E.W. Johnson et al., "Data Descriptor: MIMIC-III, a Freely Accessible Critical Caree Database", Scientific Data, 2016, 9 pgs.
Qunfeng Tang et al., "Robust Reconstruction of Electrocardiogram Using Photoplethysmography: A Subject-Based Model", Frontiers in Physiology, vol. 13, Apr. 2022, 10 pgs.
Van Gent et al., "HeartPy: A Novel Heart Rate Algorithm for the Analysis of Noisy Signals", Transportation Research Part F: Traffic Psychology and Behaviour, 2019, 13 pgs.
Van Gent et al., "Analysing Noisy Driver Physiology Real-time using Off-the-shelf Sensors: Heart Rate Analysis Software from the Taking the Fast Lane Project", Journal of Open Research Software, 2019, 10 pgs.
G. Lu et al., "A Comparison of Photoplethysmography and ECG Recording to Analyse Heart Rate Variability in Healthy Subjects", Journal of Medical Engineering & Technology, 2009, 8 pgs.
Kirstin Aschbacher et al., "Atrial Fibrillation Detection from Raw Photoplethysmography Waveforms: A Deep Learning Application", Heart Rhythm Society, 2020, 7 pgs.
Edmon Begoli et al., "The Need for Uncertainty Quantification in Machine-assisted Medical Decision Making", 2019, 7 pgs.
Thorir Mar Ingolfsson et al. "ECG-TCN: Wearable Cardiac Arrhythmia Detection with a Temporal Convolutional Network." IEEE International Conference on Artificial Intelligence Circuits and Systems (AICAS), 2021, 4 pgs.
Sajad Mousavi et al., "Inter-and intra-patient ECG Heartbeat Classification for Arrhythmia Detection: a Sequence to Sequence Deep Learning Approach." IEEE International Conference on Acoustics, Speech and Signal Processing (ICASSP), 2019, 13 pgs.
Bin Zhou et al., "BeatGAN: Anomalous Rhythm Detection using Adversarially Generated Time Series." International Joint Conference on Artificial Intelligence (IJCAI), 2019, 7 pgs.
Awni Y. Hannun et al., "Cardiologist-level Arrhythmia Detection and Classification in Ambulatory Electrocardiograms using a Deep Neural Network.", Nature Medicine Author Manuscript 25.1, 2019, 20 pgs.
Dongdong Zhang et al., "Interpretable Deep Learning for Automatic Diagnosis of 12-lead Electrocardiogram", Iscience 24.4, 2021, 22 pgs.

* cited by examiner

SYSTEM AND METHOD FOR CONTINUOUS ATRIAL FIBRILLATION DETECTION VIA PPG TO ECG SIGNAL TRANSLATION

CROSS-REFERENCE TO RELATED APPLICATION

This application claims the priority benefit under 35 U.S.C. § 119(e) of U.S. Provisional Application Nos. 63/411,914 and 63/458,303, filed on Sep. 30, 2022, and Apr. 10, 2023, respectively, the disclosure of which is incorporated by reference in its entirety as if fully set forth herein.

TECHNICAL FIELD

The disclosure generally relates to a subject-independent attention-based deep state-space model to translate photoplethysmogram (PPG) signals to corresponding electrocardiogram (ECG) waveforms. More particularly, the subject matter disclosed herein relates to improvements to the construction of an ECG signal from a PPG signal to allow for continuous atrial fibrillation (AFib) detection based on the constructed ECG signal, e.g., for wearable devices.

SUMMARY

An ECG is a medical test that measures electrical activity of the heart. ECGs are often used to diagnose and monitor a wide range of heart conditions, including arrhythmias, heart attacks, and heart failure.

Advancements in electronics, wearable technologies, and machine learning have made it possible to record ECGs more easily and accurately, and to analyze large amounts of data more efficiently. Despite these developments, there are still challenges associated with continuously collecting high-quality ECG data over an extended period, particularly in everyday life situations. For example, a 12-lead ECG, considered the clinical gold standard, and simpler versions, such as the Holter ECG, can be inconvenient and bulky due to the need to place multiple electrodes on the body, which can cause discomfort. Additionally, the signals may degrade over time as the impedance between the skin and electrodes changes.

Consumer-grade products like smartwatches have developed solutions to address these issues. However, these conventional products still require users to place their fingers on the watch to form a closed circuit, which makes continuous monitoring impossible.

An alternative to using ECG is a PPG, which uses non-invasive, low-cost optical methods to measure cardiac physiology, making it a more suitable option for capturing vital heart signs in daily life. PPG, which can be easily acquired using various wearable devices, including smartwatches, is more convenient, cost-effective, and user-friendly. As a result, PPG has become increasingly popular in health monitoring and is often used in various clinical and commercial wearable devices.

While ECG and PPG have a strong correlation, PPG does not currently offer a significant clinical diagnostic value.

Attempts have been made to synthesize ECG from PPG signals. For example, a machine learning-based approach has been proposed to estimate ECG parameters based on P, Q, R, S, and T waves, including an RR interval, PR, QRS, and QT intervals, using time and frequency domain features extracted from a fingertip PPG signal. Further, models have been proposed to reconstruct an entire ECG signal from a PPG in the frequency domain. However, the performance of these approaches relies on cumbersome algorithms for feature crafting.

With the recent advances of deep learning, attempts have been made to leverage a neural network's expressiveness and structural flexibility to build end-to-end PPG-to-ECG algorithms. However, these PPG-to-ECG algorithms are data-hungry and not robust, as deterministic models do not explicitly model the underlying sequential structures of the data. Additionally, complex deep learning models cannot run efficiently on resource-constrained devices (e.g., wearable devices) due to their high computational intensity, which poses a critical challenge for real-world deployment.

Further, continuous AFib monitoring using ECG-to-PPG translation has not been considered in the above-described works.

Additionally, using a conventional generative model may be somewhat risky as fake information may be introduced, which affects an AFib detection result. For example, CardioGAN, which is an attention-based generative adversarial network for generating ECGs, uses the synthetic generated ECG signaling for heart rate monitoring. Further, CardioGAN provides no evaluation on arrhythmias, requires a large amount of data, and requires fixed-length signals.

To overcome these issues, systems and methods are described herein for continuously performing AFib monitoring using both ECG and PPG signals.

More specifically, a generative model is provided, which incorporates prior knowledge about data structures, that enables data-efficient learning. That is, a sequential deep generative model combined with a state-space model augmented by an attention mechanism is provided. The model is inherently robust to noise because of its probabilistic nature.

Further, a subject-independent attention-based deep state-space model is provided to translate PPG signals to corresponding ECG waveforms. The model is highly data-efficient by incorporating prior knowledge in terms of probabilistic graphical models. The model may be used to detect AFib, which is one of the most common heart rhythm disorder in adults, by complementing ECG accuracy with continuous PPG monitoring.

Quantitative and qualitative experimental results demonstrate the effectiveness and efficiency of the embodiments of embodiment of the disclosure.

The above approaches improve on previous methods by providing a data efficient method (making first-order Markov relationships between segments, instead of having models learn long-term relationships like conventional models).

The above approaches also improve on previous methods by being applicable on resource constraint devices, e.g., a smart watch, by utilizing significantly fewer parameters.

The above approaches also improve on previous methods by translating in the arrhythmias contexts, i.e., do not require regular cycles.

The above approaches also improve on previous methods by providing effective AFib detection from PPG signals.

The above approaches also improve on previous methods by providing a fusion mechanism between the original ECG (when available) and the ECG translated from PPG, for AFib detection.

In an embodiment, a method is provided for AFib detection. The method includes receiving PPG signals of a user measured by a PPG sensor; translating the measured PPG signals into ECG signals using a dynamic model; analyzing the translated ECG signals using an AFib detection model, which is trained on measured ECG signals for AFib detection; and providing the analyzed AFib detection results to the user.

In an embodiment, a system is provided for AFib detection. The system includes a PPG sensor; and a processor configured to receive PPG signals of a user measured by the PPG sensor, translate the measured PPG signals into ECG signals using a dynamic model, analyze the translated ECG signals using an AFib detection model, which is trained on measured ECG signals for AFib detection, and provide the analyzed AFib detection results to the user

BRIEF DESCRIPTION OF THE DRAWING

In the following section, the aspects of the subject matter disclosed herein will be described with reference to exemplary embodiments illustrated in the figures, in which.

DETAILED DESCRIPTION

Figure 1:
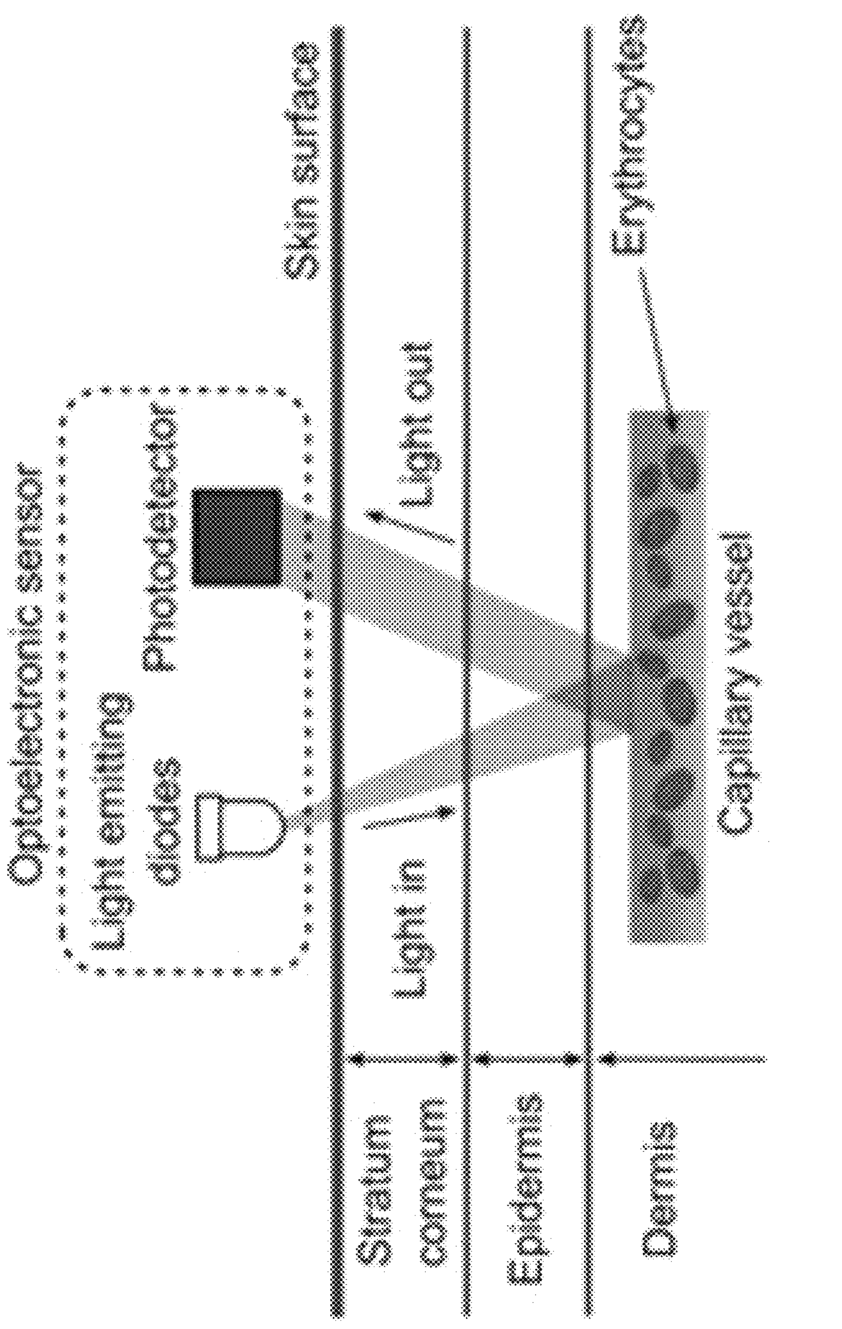
FIG. 1 illustrates a basic operation of a PPG sensor.

In the following detailed description, numerous specific details are set forth in order to provide a thorough understanding of the disclosure. It will be understood, however, by those skilled in the art that the disclosed aspects may be practiced without these specific details. In other instances, well-known methods, procedures, components and circuits have not been described in detail to not obscure the subject matter disclosed herein.

Reference throughout this specification to "one embodiment" or "an embodiment" means that a particular feature, structure, or characteristic described in connection with the embodiment may be included in at least one embodiment disclosed herein. Thus, the appearances of the phrases "in one embodiment" or "in an embodiment" or "according to one embodiment" (or other phrases having similar import) in various places throughout this specification may not necessarily all be referring to the same embodiment. Furthermore, the particular features, structures or characteristics may be combined in any suitable manner in one or more embodiments. In this regard, as used herein, the word "exemplary" means "serving as an example, instance, or illustration." Any embodiment described herein as "exemplary" is not to be construed as necessarily preferred or advantageous over other embodiments. Additionally, the particular features, structures, or characteristics may be combined in any suitable manner in one or more embodiments. Also, depending on the context of discussion herein, a singular term may include the corresponding plural forms and a plural term may include the corresponding singular form. Similarly, a hyphenated term (e.g., "two-dimensional," "pre-determined," "pixel-specific," etc.) may be occasionally interchangeably used with a corresponding non-hyphenated version (e.g., "two dimensional," "predetermined," "pixel specific," etc.), and a capitalized entry (e.g., "Counter Clock," "Row Select," "PIXOUT," etc.) may be interchangeably used with a corresponding non-capitalized version (e.g., "counter clock," "row select," "pixout," etc.). Such occasional interchangeable uses shall not be considered inconsistent with each other.

Also, depending on the context of discussion herein, a singular term may include the corresponding plural forms and a plural term may include the corresponding singular form. It is further noted that various figures (including component diagrams) shown and discussed herein are for illustrative purpose only, and are not drawn to scale. For example, the dimensions of some of the elements may be exaggerated relative to other elements for clarity. Further, if considered appropriate, reference numerals have been repeated among the figures to indicate corresponding and/or analogous elements.

The terminology used herein is for the purpose of describing some example embodiments only and is not intended to be limiting of the claimed subject matter. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being on, "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present Like numerals refer to like elements throughout. As used herein, the term "and/or" includes any and all combinations of one or more of the associated listed items.

The terms "first," "second," etc., as used herein, are used as labels for nouns that they precede, and do not imply any type of ordering (e.g., spatial, temporal, logical, etc.) unless explicitly defined as such. Furthermore, the same reference numerals may be used across two or more figures to refer to parts, components, blocks, circuits, units, or modules having the same or similar functionality. Such usage is, however, for simplicity of illustration and ease of discussion only; it does not imply that the construction or architectural details of such components or units are the same across all embodiments or such commonly-referenced parts/modules are the only way to implement some of the example embodiments disclosed herein.

Unless otherwise defined, all terms (including technical and scientific terms) used herein have the same meaning as commonly understood by one of ordinary skill in the art to which this subject matter belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "module" refers to any combination of software, firmware and/or hardware configured to provide the functionality described herein in connection with a module. For example, software may be embodied as a software package, code and/or instruction set or instructions, and the term "hardware," as used in any implementation described herein, may include, for example, singly or in any combination, an assembly, hardwired circuitry, programmable circuitry, state machine circuitry, and/or firmware that stores instructions executed by programmable circuitry. The modules may, collectively or individually, be embodied as circuitry that forms part of a larger system, for example, but not limited to, an integrated circuit (IC), system on-a-chip (SoC), an assembly, and so forth.

Herein, the terms "an ECG signal" and "a PPG signal" may also be respectively referred to as "an ECG" or "a PPG".

Conventional ECG measurement devices are bulky and inconvenient, since placing multiple electrodes on a body usually causes discomfort and the signals deteriorate over time, which restricts long-term use of the ECG measurement devices. Although there are some medical devices that can provide long-term ECG monitoring, they are relatively expensive and not widely used. Additionally, conventional smartwatches can only perform intermittent ECG measurements, i.e., requiring users to put a finger on the crown to close the loop.

FIG. 1 illustrates a basic operation of a PPG sensor.

Referring to FIG. 1, a PPG sensor uses an optical technique to detect volumetric changes in blood in peripheral circulation. More specifically, a PPG sensor measures an amount of light that is absorbed or reflected by blood vessels in living tissue. This technique involves the use of a light source, usually a light emitting diode (LED), and a photodetector to measure the changes in light absorption or reflection as blood flows through the tissue. As illustrated, light is emitted from the LED onto and through a skin surface. The emitted light may reflect off a capillary vessel and is then detected and measured by a photodetector.

PPG technology as illustrated in FIG. 1 represents a convenient and low-cost technology, which is commonly used in pulse oximetry in clinical settings for measuring oxygen saturation. PPG sensors are often available in many wearable devices, e.g., from low-end to high-end smartwatches. Although the PPG sensors on smartwatches are currently only used for measuring heart rate, there is potential to analyze morphologies of PPG waveforms to infer different cardiovascular information.

More specifically, ECG and PPG signals are inherently correlated as both are influenced by the same underlying cardiac activity, namely the depolarization and repolarization of the heart. These contractions lead to changes in peripheral blood volume, which are measured by PPG.

Although there are established standards for interpreting ECG for clinical diagnosis, the use of PPG is still mostly limited to measuring heart rate and oxygen saturation. By translating PPG to ECG signals, clinical diagnoses of cardiac diseases and anomalies can be made in real-time.

Figure 2:
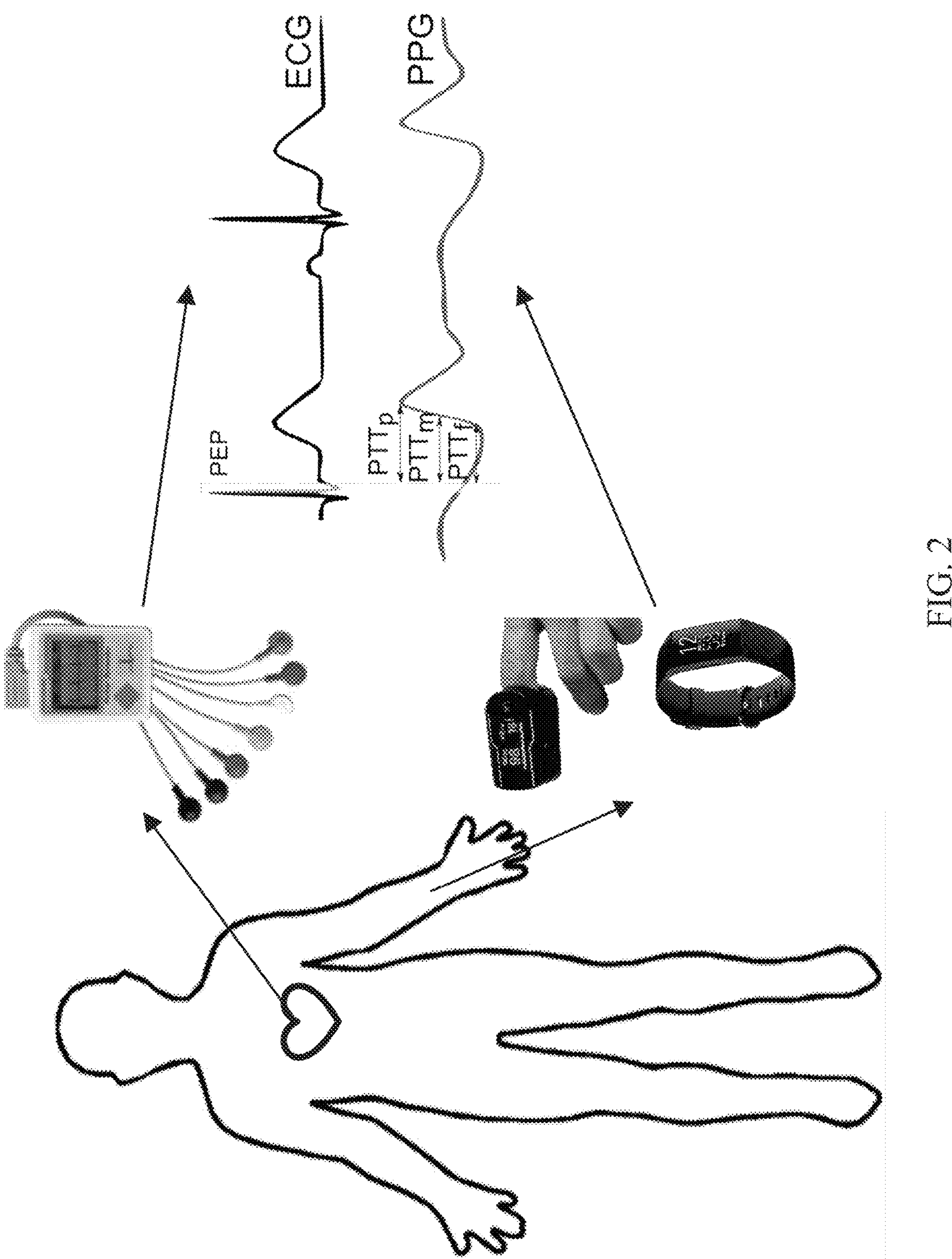
FIG. 2 illustrates a relationship of PPG and ECG signals.

FIG. 2 illustrates a relationship of PPG and ECG signals.

Referring to FIG. 2, physiologically, PPG and ECG signals are correlated, considering that a variation of peripheral blood volume is influenced by ventricular activities. The timing, amplitude, and shape characteristics of PPG waveforms contain information about the interaction between the heart and connective vasculature.

For the heart to contract and pump blood, a series of coordinated electrical signals are generated. These heart contractions cause variations in peripheral blood volume, which are measured by the PPG. The pre-ejection period (PEP) is the time elapsed between the electrical depolarization of the left ventricle and the beginning of ventricular ejection. Pulse transit time (PTT) is defined as the period from a relatively proximal site (e.g., arm) to a distal site (e.g., finger) or between two distal sites (e.g., figure and toe). The pulse arrival time (PAT) is the time it takes for the pulse to travel from the heart to a peripheral artery. The PAT interval includes the PTT interval plus the PEP.

Although ECG, with PQRST waves, arguably provides more information, especially, for diagnosis in clinical practice, PPG may be more convenient, economical, and easier to use, especially, in daily life. Accordingly, PPG measurement capabilities and devices are increasingly being included in consumer electronics such as wearable devices, e.g., smartwatches, that deliver continuous and long-term monitoring capabilities.

While the present disclosure mainly refers to the use of a smartwatch that provides a PPG device on a user's wrist, the disclosure is also applicable to other types of PPG devices that can be attached to earlobes, fingertips, and/or other body areas.

Additionally, while the present disclosure mainly describes PPG-to-ECG translation for AFib detection, embodiments of the disclosure may also be used to make other clinical diagnoses of cardiac diseases and detect other anomalies in real-time detect.

Although PPG is becoming more popular for health monitoring, ECG is still considered the gold standard for medical diagnosis and vital sign monitoring. While standards in interpreting ECG have long been established, the vast use of PPG is still limited, and thus it is mostly used for monitoring a heartrate and pulse oximetry.

In accordance with an embodiment of the disclosure, the close correlation between ECG and PPG is used to develop an efficient method for synthesizing ECG from PPG waveform, providing an economical and user-friendly ECG screening for continuous and long-term monitoring. This method takes advantage of both the rich clinical knowledge base of ECG in many instances, ranging from well-established ECG-based arrhythmia detection and abnormalities of heartbeat in unhealthy patients, focal causes of atrial fibrillation, and ventricular tachycardias, as well as the convenience and accessibility of PPG in daily settings.

For example, by synthesizing ECG from PPG signals acquired through currently available wearable devices, clinical diagnoses of cardiac diseases and anomalies can be done in real time, 24/7, anywhere, and ideally with the aid of machine learning and cloud computing.

Accordingly, the present disclosure provides a generative model incorporating prior knowledge about the data structures that enable data-efficient learning, i.e., a sequential deep generative model combined with a state-space model augmented by an attention mechanism, which is inherently robust to noise because of its probabilistic nature. This may be demonstrated by evaluating the model on data corrupted with Gaussian and baseline wandering noise, mimicking real-world scenarios.

Figure 3:
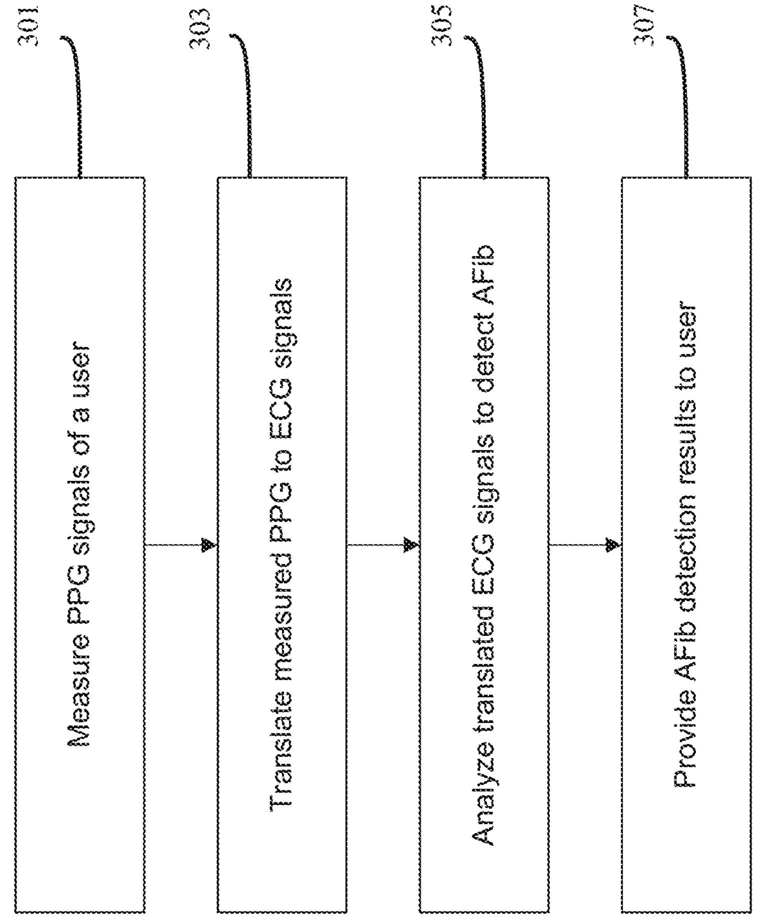
FIG. 3 is a flow chart illustrating a method of AFib detection according to an embodiment.

FIG. 3 is a flow chart illustrating a method of AFib detection according to an embodiment.

Referring to FIG. 3, in step 301, PPG signals of a user are measured, e.g., using a smartwatch.

In step 303, the measured PPG signal are translated to ECG signals using a dynamic model according to an embodiment of the disclosure.

In step 305, the translated ECG signals are analyzed using a AFib detection model, which is trained on measured ECG signal for AFib detection, e.g., a Multilevel Knowledge-Guided Attention (MINA) model, which predicts heart diseases from ECG signals.

In step 307, the analyzed AFib detection results are provided to the user. For example, an indication of the results may be displayed on a screen of the smartwatch.

Additionally or alternatively, the analyzed AFib detection results may be provided via messaging, email, etc., to an authorized individual, such as a doctor, parent, spouse, etc., of the user.

Dynamical Model to Translate PPG Signals to ECG Signals and Latent Factors of Data Variations Probabilistic Modeling of ECG from PPG Signals Consider a data set of PPG-ECG pairs:

$$D := \{(x^1, y^1), \ldots, (x^N, y^N)\}$$

with the i-th observation $y^i$, ECG signals of $n_y$ time samples, depending on PPG signals $x^i$ of $n_x$ time samples. Herein, the superscript i may be omitted when referring to only one sequence or when it is clear from the context.

In accordance with an embodiment, the PPG-to-ECG translation aims to learn a generative process with a latent-variable model including a parametric non-linear Gaussian prior over latent variables $p_\theta(z|x)$ and likelihood $p_\theta(y|z, x)$. As shown in Equation (1), the learning process minimizes a divergence between the true data-generating distribution D and the model w.r.t θ:

$$\underset{\theta}{\operatorname{argmin}} KL(p_D(y \mid x) \| (p_\theta(y \mid x)) = \underset{\theta}{\operatorname{argmax}} E_{p_D(y|x)}[\log p_\theta(y \mid x)] \quad (1)$$

In Equation (1), $$p_\theta(y \mid x) = \int p_{\theta_y}(y \mid z, x) p_{\theta_z}(z \mid x) dz$$

is conditional likelihood/evidence of data point y given condition x, approximated by integrating over the latent z, and KL(p||q) calculates the Kullback-Leibler (KL) divergence between two probability distributions p and q.

Nevertheless, estimating $p_\theta(y|x)$, is typically intractable. This issue can be mitigated by introducing a parametric inference model $q_\phi(z|x, y)$ to construct a conditional variational evidence lower bound on the conditional log-likelihood log $p_\theta(y|x)$ as shown in Equation (2).

$$\mathcal{L}_{C\text{-}VAE}(x, y; \theta, \phi) = -KL(q_\phi(z \mid x, y) \| p_{\theta_z}(z \mid x)) + E_{q_\phi}(z \mid x, y)\left[\log p_{\theta_y}(y \mid z, x)\right] \quad (2)$$

Given observation variables (PPG/ECG segments) and corresponding latent variables z, their generating processes are definable as $$z \sim p(z) = \mathcal{N}(0, I) \text{ and } x \sim p_\theta(x|z),$$

where θ is the model parameter of p, $q_\phi(z|x)$ is an approximate distribution of posterior p(z|x), and ϕ is the model parameter of q.

$q_\phi(z|x, y)$ is designated as an encoder, the likelihood model $p_{\theta_y}(y|z, x)$ is designated as a decoder, and $p_{\theta_z}(z|x)$ is designated as the prior model.

To optimize the lower bound $\mathcal{L}_{C\text{-}VAE}$ with respect to model (or neural network) parameters θ and ϕ, gradients of Equation (2) are estimated using stochastic gradient variational Bayes (SGVB).

If $q_\phi(z|x)$ is considered as a Gaussian distribution $\mathcal{N}$ (z; μ, diag($\sigma^2$)), where ϕ={μ, $\sigma^2$}, then z~$q_\phi(z|x)$ can be re-parameterized to $$z = \mu + \sigma \odot \epsilon, \text{ where } \epsilon \sim \mathcal{N}(0, I).$$

Therefore, gradients of the negative reconstruction term in Equation (2) can be estimated with respect to θ and ϕ as $$\nabla_{\theta,\phi} E_{q_\phi(z|x)}[\log\ p_\theta(x|z)] = E_{N(\epsilon;0,I)}[\nabla_{\theta,\phi} \log\ p_\theta(z|\mu + \sigma \odot \epsilon)].$$

Because the gradients of the regularization term are solvable analytically, Equation (2) can be optimized with standard stochastic optimization methods.

State-Space Modeling of ECG from PPG Signals

In accordance with an embodiment, neural network design may be used to model a time-series, while taking into account a quasi-periodic nature of physiological signals.

ECG Generative (Decoding) Process from PPG

In an ECG generative (decoding) process from a PPG, non-linear dynamical systems with ECG observations $y_t$ in RR intervals or a time elapsed between two successive R peaks on the ECG are considered, depending on control PPG inputs $x_t$ in PP intervals or the time elapsed between two successive systolic peaks on the PPG. Peaks are chosen to segment the signals as they are the most robust features. Corresponding discrete time sequences of length T are denoted as $$y_{1:T} = (y_1, y_2, \ldots, y_T) \text{ and } x_{1:T} = (x_1, x_2, \ldots, x_T).$$

Given an input PPG $x_{1:T}$, a probabilistic model $p(y_{1:T}|x_{1:T})$ is intended. Formally, the graphical model shown in Equation (3) is assumed.

$$p(y_{1:T}|x_{1:T}) = \int p(y_{1:T}|z_{1:T}, x_{1:T}) p(z_{1:T}|x_{1:T}) dz_{1:T} \quad (3)$$

In Equation (3), $z_{1:T}$ denotes the corresponding latent sequence. That is, a generative model is assumed with an underlying latent dynamical system with emission model $p(y_{1:T}|z_{1:T}, x_{1:T})$ and transition model $p(z_{1:T}|x_{1:T})$.

To obtain state-space models, Markovian assumptions are imposed on state transition and emission models, as shown in Equations (4) and (5) below, where it is assumed that the current state $z_t$ contains all necessary information about the current observation $y_t$, as well as the next state $z_{t+1}$ (given the current control input $x_t$). That is, as opposed to observations, $z_t$ exhibits Markovian behavior.

$$p(z_{1:T} \mid x_{1:T}) = \prod_{t=0}^{T-1} p(z_{t+1} \mid z_t, x_{1:T}) \tag{4}$$

$$p(y_{1:T} \mid z_{1:T}, x_{1:T}) = \prod_{t=1}^{T} p(y_t \mid z_t) \tag{5}$$

Figure 4:
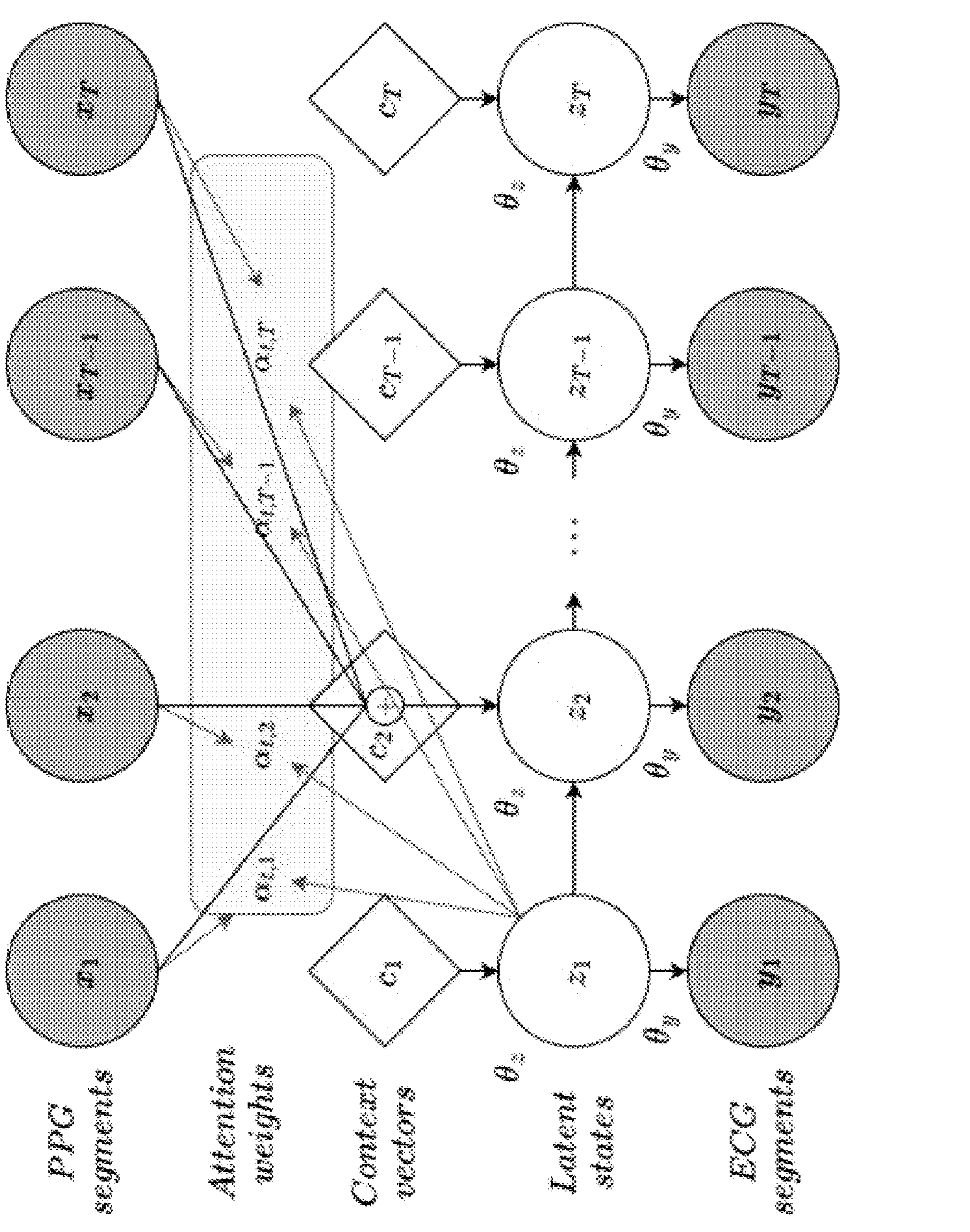
FIG. 4 illustrates a graphical model for ECG translation from PPG according to an embodiment.

FIG. 4 illustrates a graphical model for ECG translation from PPG according to an embodiment.

Referring to FIG. 4, shaded nodes represent observed variables. Clear nodes represent latent variables. Diamond nodes denote deterministic variables. Variables $x_t$, $y_t$, and $c_t$ represent PP intervals, RR intervals, and context vectors, respectively. $\alpha_{t,i}$ are attention weights that define how well two intervals $x_i$ and $y_t$ are aligned. The attention mechanism is shown as an example at time step 2.

This disclosed model takes into account an entire input signal $x_{1:T}$ for each output $y_t$ via an attention mechanism. There are usually misalignments between PPG and ECG cycles. Therefore, it is often difficult to construct optimal and exact sample pairs. The attention mechanism helps to cope with the misalignment problem and adds more context for the generation of ECG segments.

As shown in Equation (6) below, $c_t$ may be defined a sum of features of the input sequence (PP intervals), weighted by the alignment scores.

$$c_t = \sum_{i=1}^{T} \alpha_{t,i} x_i \tag{6}$$

$$\alpha_{t,i} = \frac{\exp(s(z_{t-1}, x_i))}{\sum_{i'=1}^{n} \exp(s(z_{t-1}, x_{i'}))} \tag{7}$$

In Equation (7), the alignment function s assigns a score $\alpha_{t,i}$ to the pair of inputs at position i and output at position t, $(x_i, y_t)$, based on how well they match. The set of $\alpha_{t,i}$ are weights defining how much of each source segment should be considered for each output interval.

The state transition (prior) and emission models as shown in Equations (8) and (9) are assumed to be non-linear Gaussian transformations.

$$p_{\theta_z}(z_{t+1} \mid z_t, x_{1:T}) = N\left(z_{t+1} \mid \mu_{\theta_z}(z_t, c_{t+1}), \sigma^2_{\theta_z}(z_t, c_{t+1})\right) \tag{8}$$

$$p_{\theta_y}(y_t \mid z_t) = N\left(y_t \mid \mu_{\theta_y}(z_t), I\right) \tag{9}$$

In Equations (8) and (9), $\mu$ and $\sigma^2$ are the means and diagonal covariance matrices of the normal distributions N, and I is an identity covariance matrix.

Latent State Inference (Posterior Encoding) Process

Unlike a deterministic translation model, the process is used to find meaningful probabilistic embeddings of ECG segments in the latent space. For example, a goal is to identify the structure of a posterior distribution $p_\theta(z_{1:T} \mid y_{1:T})$. Here, a design choice is made to perform inference using only $y_{1:T}$, with an assumption that the PPG segments do not provide more information than ECG segments alone. Applying the chain rule allows the distribution to be rewritten as shown in Equation (10).

$$p_\theta(z_{1:T} \mid y_{1:T}) = p_\theta(z_1 \mid y_{1:T}) \prod_{t=1}^{T-1} p_\theta(z_{t+1} \mid z_{1:t}, y_{1:T}) \tag{10}$$

Thereafter, the Markovian property may be used to simplify each term in the product.

The structure illustrated in FIG. 4 shows that $z_t$ node blocks all information coming from the past and flowing to $z_{t+1}$ (i.e., $z_{1:t-1}$ and $z_{1:t}$). That is, $z_t$ has accumulated all past information or is a summary of this information. Thus, $$p_\theta(z_{t+1} \mid z_{1:T}, y_{1:T}) = p_\theta(z_{t+1} \mid z_t, y_{t+1:T}).$$

In view of this, Equation (10) can be rewritten as Equation (11).

$$p_\theta(z_{1:T} \mid y_{1:T}) = p_\theta(z_1 \mid y_{1:T}) \prod_{t=1}^{T-1} p_\theta(z_{t+1} \mid z_t, y_{t+1:T}) \tag{11}$$

Figure 5:
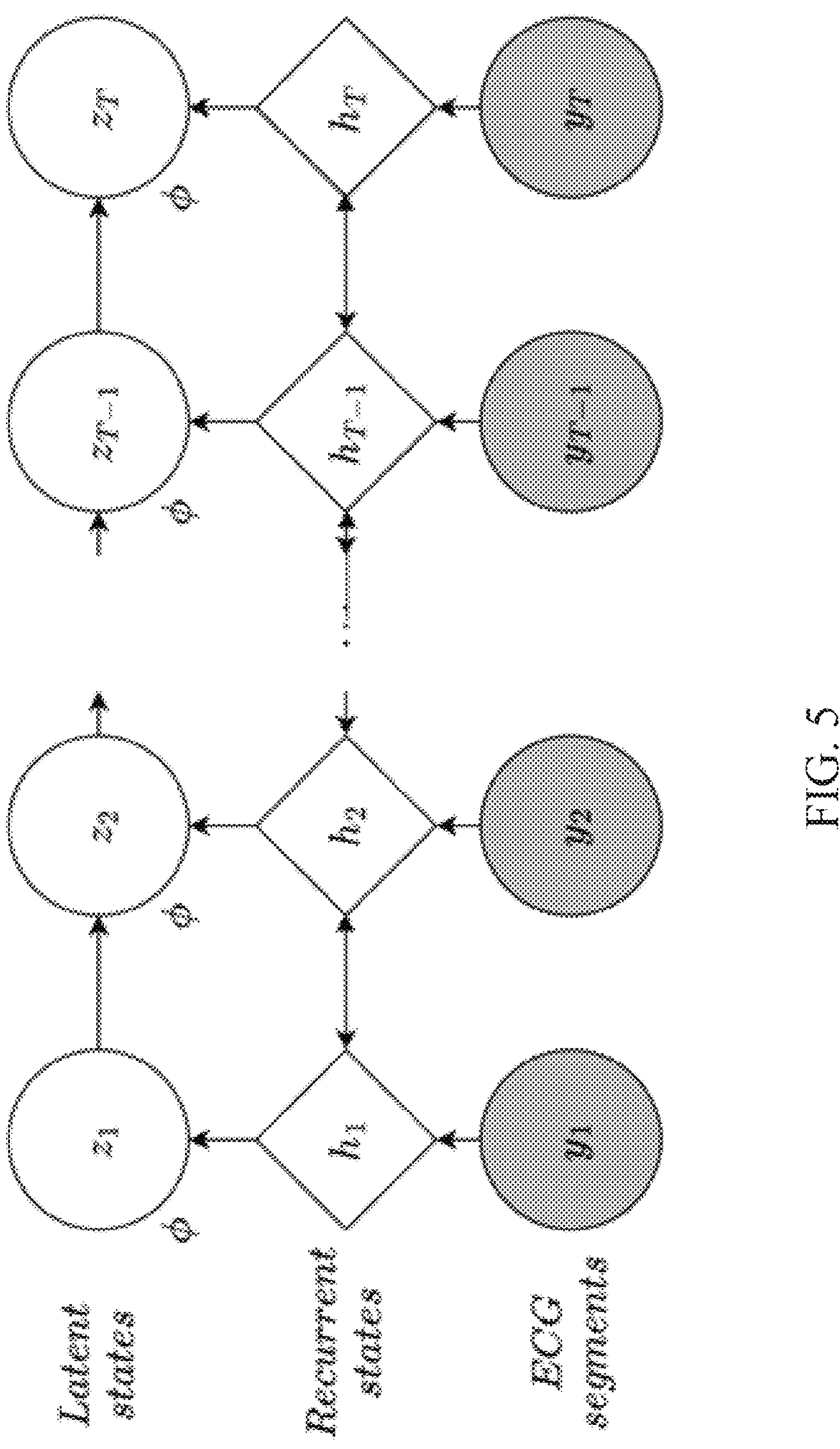
FIG. 5 illustrates a graphical model at latent state inference time according to an embodiment.

FIG. 5 illustrates a graphical model at latent state inference time according to an embodiment.

Referring to FIG. 5, the variables $y_t$, $h_t$, and $z_t$ represent respectively RR intervals, bidirectional recurrent states, and latent states.

The variational approximation of the posterior factorizes according to the structure of the exact posterior as illustrated in FIG. 5 as shown in Equations (12) and (13).

$$q_\phi(z_{1:T} \mid y_{1:T}) = q_\phi(z_1 \mid y_{1:T}) \prod_{t=1}^{T-1} q_\phi(z_{t+1} \mid z_t, y_{t+1:T}) \tag{12}$$

$$q_\phi(z_{t+1} \mid z_t, y_{t+1:T}) = N\left(z_{t+1} \mid \mu_{\theta_2}(z_t, y_{t+1:T}), \sigma^2_\phi(z_t, y_{t+1:T})\right) \tag{13}$$

Training Process

Figure 6:
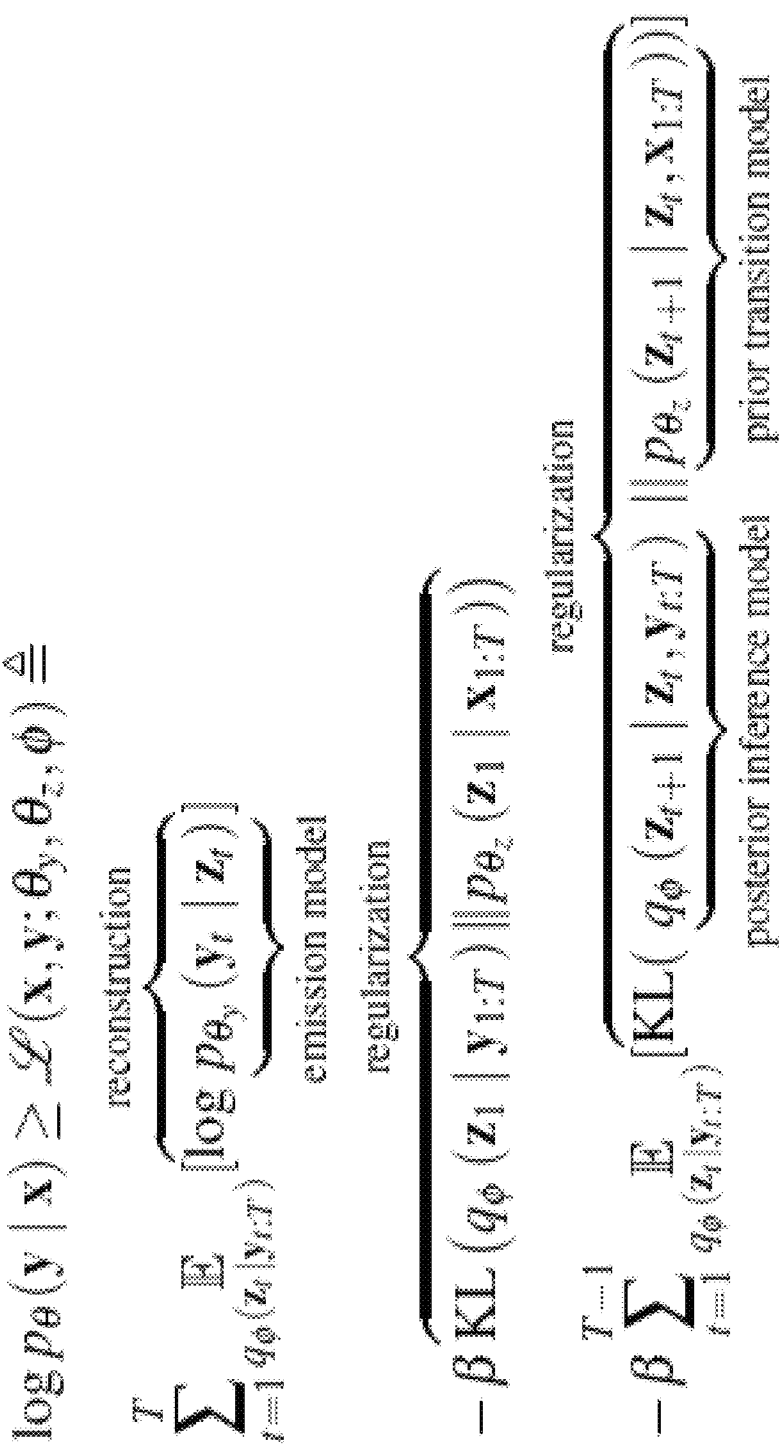
FIG. 6 illustrates a timestep-wise conditional variational lower bound according to an embodiment.

FIG. 6 illustrates a timestep-wise conditional variational lower bound according to an embodiment. More specifically, the timestep-wise conditional variational lower bound of FIG. 6 will be used as the objective function for neural network training, where $\beta$ controls the strength of the regularization terms.

Referring to FIG. 6, the objective function for neural network training becomes a timestep-wise conditional variational lower bound. During training, KL losses in the regularization terms "pull" the posterior distributions (which encode ECG segments) and the prior distributions (which embed PPG segments) towards each other. As in a conditional variational autoencoder (CVAE), the generative and inference models are jointly learned by maximizing the conditional variational lower bound with respect to their parameters.

Neural Network Parametrization

Below, W, v, and b denote weight matrices of the neural networks.

Score Model: The alignment score $\alpha$ in Equation (7) above is parametrized by a feed-forward network with a single hidden layer, and this network is jointly trained with other parts of the model. The score function s is therefore in the form as shown in Equation (14).

$$s(z_{t-1}, x_i) = v_s^T \tanh(W_s[z_{t-1}; x_i] + b_s) \quad (14)$$

Prior Transition Model: The transition function in Equation (8) may parameterized from $z_t$ to $z_{t+1}$ using a Gated Transition Function. The model is flexible in choosing a nonlinear transition for some dimensions while having linear transitions for others. The function may be parametrized as shown in Equation (15).

$$g_t = \text{sigmoid}\,(W_{g2}\ ReLU(W_{g1}[z_t; c_{t+1}] + b_{g1}) + b_{g2}) \quad (15)$$

$$d_t = W_{d2}\ ReLU(W_{d1}[z_t; c_{t+1}] + b_{d1}) + b_{d2}$$

$$\mu_{\theta_z}(z_t, c_{t+1}) = (1-g) \odot (W_{\mu_z}[z_t; c_{t+1}] + b_{\mu_z}) + g_t \odot d_t$$

$$\sigma^2_{\theta_z}(z_t, c_{t+1}) = \text{softplus}\left(W_{\sigma_z^2} ReLU(d_t) + b_{\sigma_z^2}\right)$$

In Equation (15), $g_t$ denotes a latent variable in a gated transition network, ReLU denotes a rectified linear unit, and $\odot$ denotes element-wise multiplication.

Emission Model: The emission function in Equation (9) may be parametrized using a two-hidden layer network as shown in Equation (16).

$$\mu_{\theta_y}(z_t) = W_{e3} ReLU(W_{e2} ReLU(W_{e1} z_t + b_{e1}) + b_{e2}) + b_{e3} \quad (16)$$

Posterior Inference Model: A gated recurrent unit (GRU) network may be used to process the sequential order of RR intervals backward from $y_T$ to $y_{t+1}$. The GRU is denoted here as $$h_t = GRU(y_T, \ldots, y_{t+1}).$$

The hidden states of the GRU parametrize the variational distribution, which are combined with the previous latent states for the inference as shown in Equation (17).

$$\tilde{h}_t = \frac{1}{2}(\tanh(W_h z_t + b_h) + h_t) \quad (17)$$

$$\mu_\phi(z_t, y_{t+1:T}) = W_\mu \tilde{h}_t + b_\mu$$

$$\sigma^2_\phi(z_t, y_{t+1:T}) = \text{softplus}(W_{\sigma^2} \tilde{h}_t + b_{\sigma^2})$$

Alternatively, a bi-directional GRU network may be used to process the sequential order of RR intervals backward from $y_T$ to $y_{t+1}$ and forward from $y_{t+1}$ to $y_T$. Here, the GRUs are may be denoted as $$h_t = GRU(W_y y_T, \ldots, W_y y_{t+1}) \text{ and } g_t = GRU(W_y y_{t+1}, \ldots, W_y y_T),$$

respectively. The hidden states of the GRUs parametrize the variational distribution, which are combined with the previous latent states for the inference as shown in Equation (18).

$$\tilde{h}_t = \frac{1}{3}(\tanh(W_h z_t + b_h) + h_t + g_t) \quad (18)$$

-continued $$\mu_\phi(z_t, y_{t+1:T}) = W_\mu \tilde{h}_t + b_\mu$$

$$\sigma^2_\phi(z_t, y_{t+1:T}) = \text{softplus}(W_{\sigma^2} \tilde{h}_t + b_{\sigma^2})$$

Implementation Scenarios and Experimental Results

Data Pre-Processing

Figure 7:
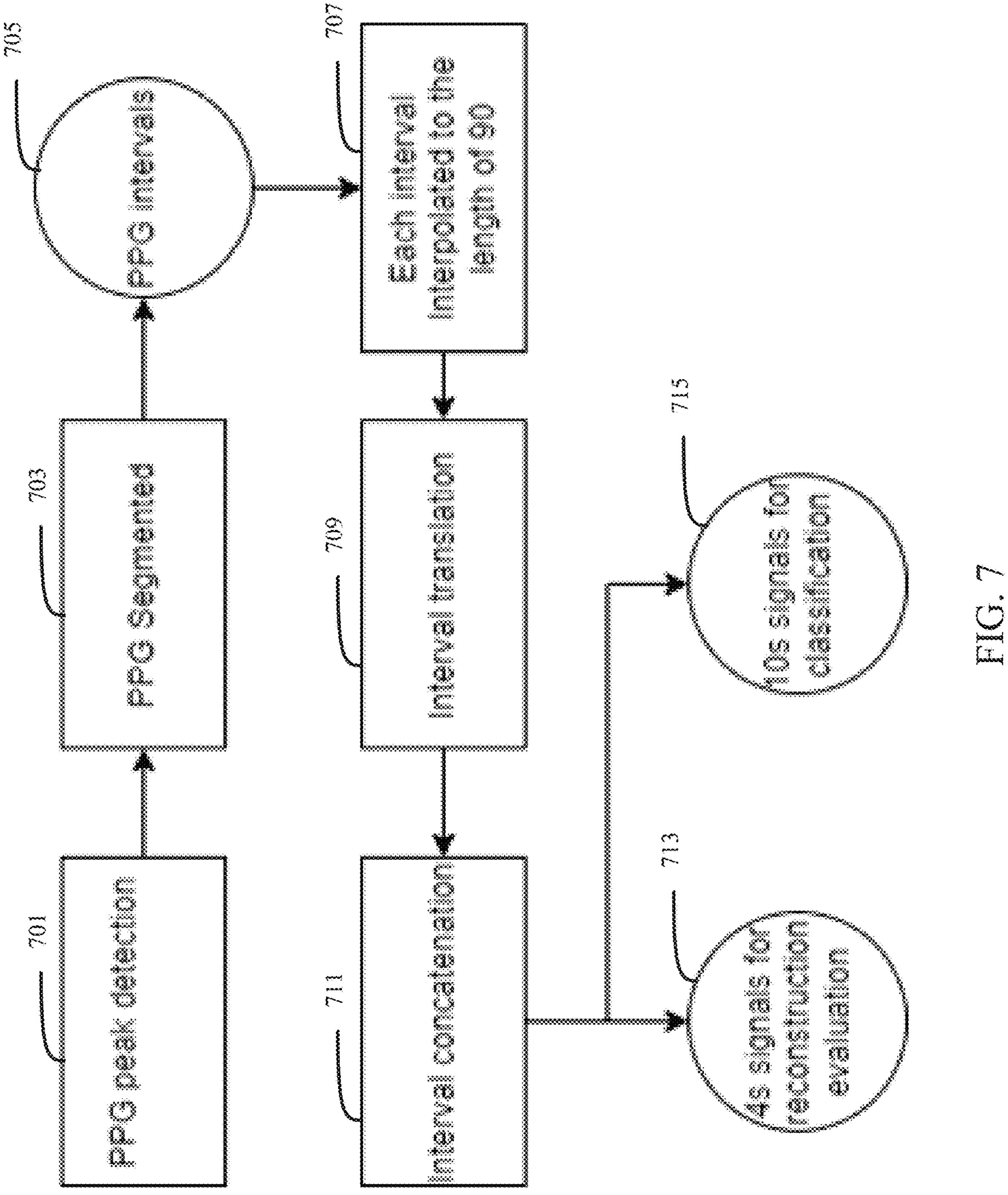
FIG. 7 illustrates a process of generating an ECG signal from a PPG signal according to an embodiment.

FIG. 7 illustrates a process of generating an ECG signal from a PPG signal according to an embodiment.

Referring to FIG. 7, data pre-processing, e.g., processing raw measured data before actually training on it or doing any inference on it, includes a filtering stage, an alignment I stage, a normalization stage, a data splitting stage, a peak-to-peak interval extraction stage, and an artificial noise addition stage.

In step 701, PPG peak detection is performed.

More specifically, in the filtering stage, the ECG and PPG signals are filtered by a fourth-order Chebyshev II filter. The frequency range of the filter used in the ECG is 0.5-20 Hz and the frequency range in the PPG is 0.5-10 Hz.

In the alignment I stage, the R peak and systolic peak are main features in the ECG and PPG signals, respectively. For each R peak in an ECG signal, the corresponding systolic peak in the PPG is the one between the current and next R peaks in the ECG. A Pan-Tompkin method may be used to detect the R peaks in the ECG, and a block method may be used to detect the systolic peaks in the PPG. Subsequently, a third systolic peak in the PPG may be aligned to the corresponding R peak in the ECG. Herein, the alignment process includes aligning the systolic peak of the PPG beat with the R peak of the ECG beat.

In the normalization stage, after alignment I, the PPG signals are scaled to [0,1]. The aligned ECG is not normalized so that the predicted ECG can be compared with the reference ECG.

In step 703, the PPG is segmented.

More specifically, in the dataset splitting stage, to evaluate long-term performance of the model, the first 60 seconds of the aligned signal are used to train and validate, while others are used to test. The alignment I step causes the length of the aligned signals to be less than 300 seconds and the length of each record to be inconsistent.

In step 705, PPG intervals are identified.

More specifically, in the peak-to-peak interval extraction stage, each PP interval of the PPG signal is extracted to be translated to a corresponding RR interval of the ECG signal.

In step 707, all intervals are linear interpolated to the length of 90, which is a mean length of the intervals on the training set.

In step 709, the PP intervals are translated to corresponding RR intervals of a translated ECG signal. The PP interval lengths are used as RR interval lengths on reconstructed ECG signals.

In the artificial noise addition stage, amplitudes of baseline noise signals are 0.3, 0.4, and 0.1, and the frequencies are 0.3 Hz, 0.2 Hz, and 0.9 Hz, respectively. Gaussian noise has a standard deviation 0.3.

Figure 8:
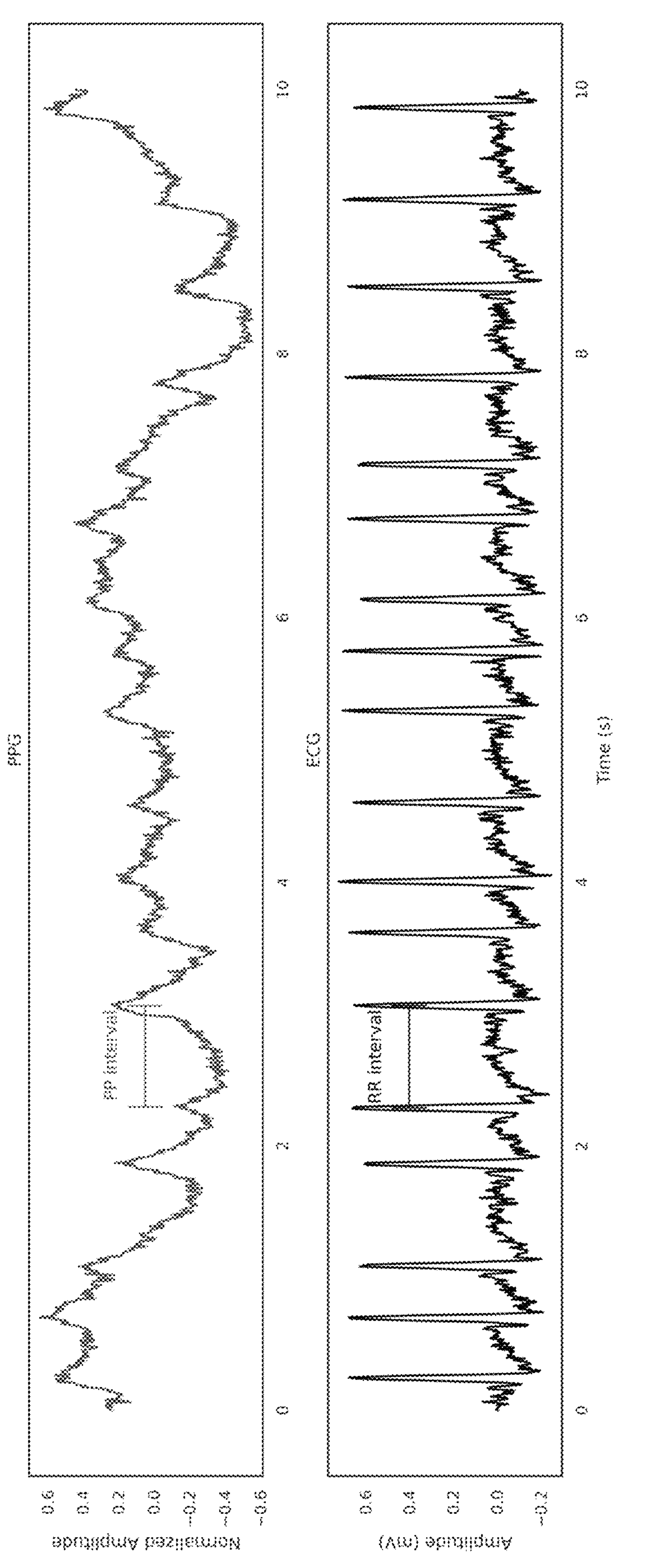
FIG. 8 illustrates a pre-processing result on noisy data according to an embodiment.

FIG. 8 illustrates a pre-processing result on noisy data.

In step 711, the translated TR intervals are concatenated to form a translated ECG signal.

More specifically, in step 713, the translated TR intervals are concatenated to form 4 second translated ECG signals for reconstruction evaluation, and in step 715, the translated TR intervals are concatenated to form 4 second translated ECG signals for classification.

After the translated ECG signals are generated from the measured PPG signals, to perform AFib detection, the translated ECG signals are applied to an AFib detection model, which is trained on real ECG signals for AFib detection, e.g., a MINA model.

ECG-PPG Fusion for AFib Detection

Figure 9:
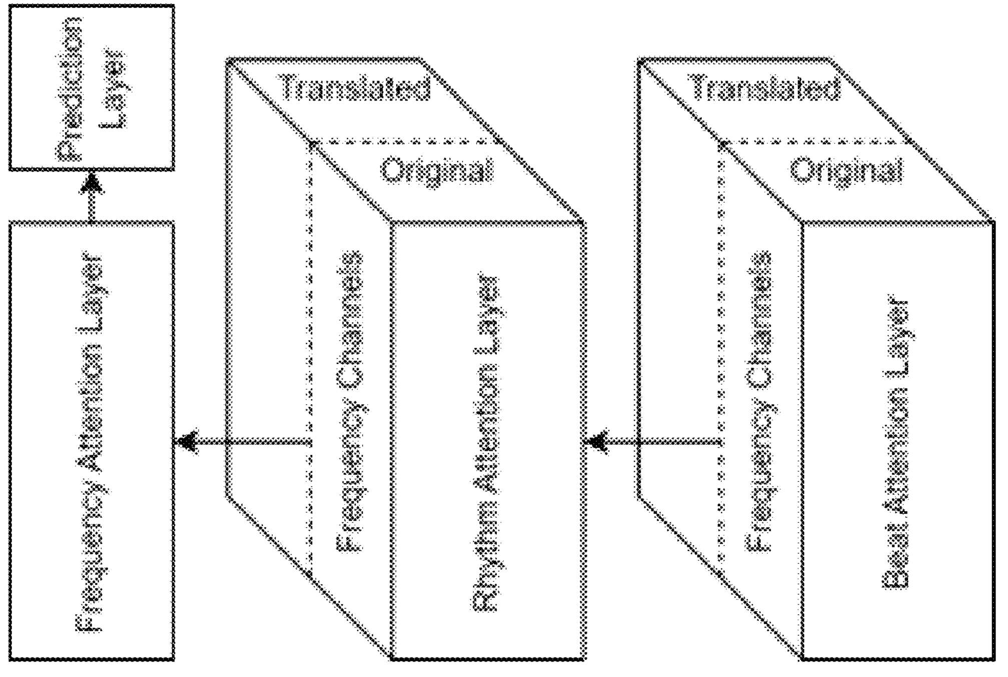
FIG. 9 illustrates an extended AFib detection model modified for AFib detection on both translated and original ECG signals according to an embodiment.

FIG. 9 illustrates an extended AFib detection model modified for AFib detection on both translated and original ECG signals according to an embodiment.

Referring to FIG. 9, an AFib detection model is modified to concatenate both real ECG features and translated PPG-to-ECG features, where the real ECG signals are available only a percentage of the time, but the PPG-to-ECG signals are available all the time. The network architecture may also be modified to concatenate both features.

In FIG. 9, the MINA model capability is extended to receive both real and translated ECG signals by incorporating the frequency channels of the translated into the model. This scenario is when both ECG and PPG signals can be measured simultaneously. This setting uses retraining of the MINA model on the fused real and synthetic ECG signal dataset. To simulate the real-life setting where ECG measurement is intermittent while PPG input is continuous, random time samples are zeroed out with different probabilities: 30%, 50%, and 70%. The higher the discontinuity, the worse the performance for the detection on real ECG, but the performance remains almost unchanged in the fusion mode. The fusion model consistently outperforms the single-modality model across the omission thresholds. Also, the model learns to utilize sparse real ECG to marginally improve the performance against only translated ECG. This suggests our model's enhancement for the downstream task in real-time AFib detection.

In accordance with another embodiment of the disclosure, by using a priori information on whether an ECG signal is available or not, selection fusion may utilize the ECG signal solely when it is available for AFib detection. However, when the ECG is not available, the system will switch to AFib monitoring using the translated PPG-to-ECG signal, where the PPG-to-ECG signal is the translated (or synthetic) ECG signal obtained using a PPG-to-ECG translation method as described above.

As shown in Table 1 below, if ECG is available T % of time only, the expected average accuracy is as shown in Equation (19).

$$\text{Selection Fusion Accuracy} = T\% \times \text{Real ECG accuracy} + (1 - T\%) \times \text{Translated ECG accuracy} \quad (19)$$

In the AFib detection performance shown in Table 1, the performance on the translated ECG is evaluated when the MINA model is trained on real ECG, but tested on synthetic ECG. The fusion performance is when the MINA model is extended to receive both real ECG and synthetic ECG inputs. x % random time samples are omitted, simulating intermittent ECG recording, while synthetic ECG is always available This selection fusion method allows continuous AFib monitoring, while achieving satisfactory detection performance. For example, at T %=70%, AFib monitoring with ECG signals is available for only 30% of the time, will yield F1-score of 0.846, while selection fusion is expected to yield an F1-score 0.3×0.985+0.7×0.944=0.9563. This demonstrates that continuous AFib monitoring with selection fusion between available ECG and continuous PPG-to-ECG signals is better than AFib monitoring with only measured ECG signals.

TABLE 1

| | Real ECG | Translated ECG | Fusion |
|---|---|---|---|
| | 0.995 ± 0.006 | 0.99 ± 0.004 | |
| | 0.987 ± 0.013 | 0.986 ± 0.007 | |
| | 0.985 ± 0.009 | 0.944 ± 0.014 | |
| | Real ECG - 30% missing | Real ECG - 50% missing | Real ECG - 70% missing |
| AUROC | 0.983 ± 0.009 | 0.982 ± 0.016 | 0.958 ± 0.021 |
| AUPRC | 0.962 ± 0.015 | 0.957 ± 0.044 | 0.931 ± 0.041 |
| F1 | 0.96 ± 0.019 | 0.929 ± 0.017 | 0.871 ± 0.037 |
| | Fusion - 30% missing | Fusion - 50% missing | Fusion - 70% missing |
| | 0.992 ± 0.006 | 0.99 ± 0.006 | 0.99 ± 0.009 |
| | 0.986 ± 0.011 | 0.982 ± 0.012 | 0.981 ± 0.016 |
| | 0.971 ± 0.01 | 0.969 ± 0.012 | 0.956 ± 0.046 |

Figure 10:
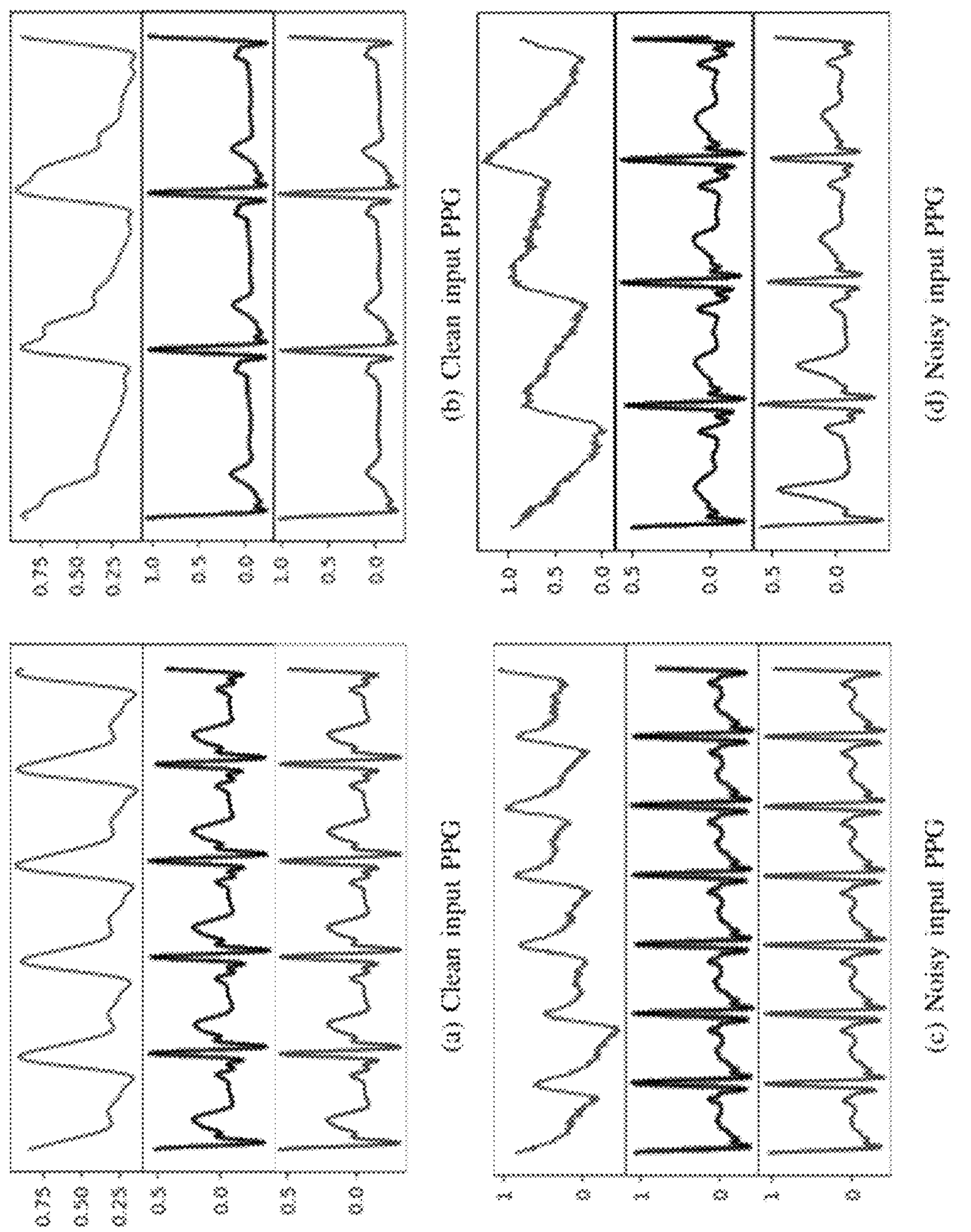
FIG. 10 illustrates examples of translated ECG signals according to an embodiment.

FIG. 10 illustrates examples of translated ECG signals according to an embodiment.

Referring to FIG. 10, in each of subfigures (a), (b), (c), and (d), from top to bottom, a reference PPG, a reference ECG, and a translated ECG are provided. Each signal is 4 seconds in length. The amplitudes of PPG signals are normalized, while the amplitudes of ECG signals are in mV.

Figure 11:
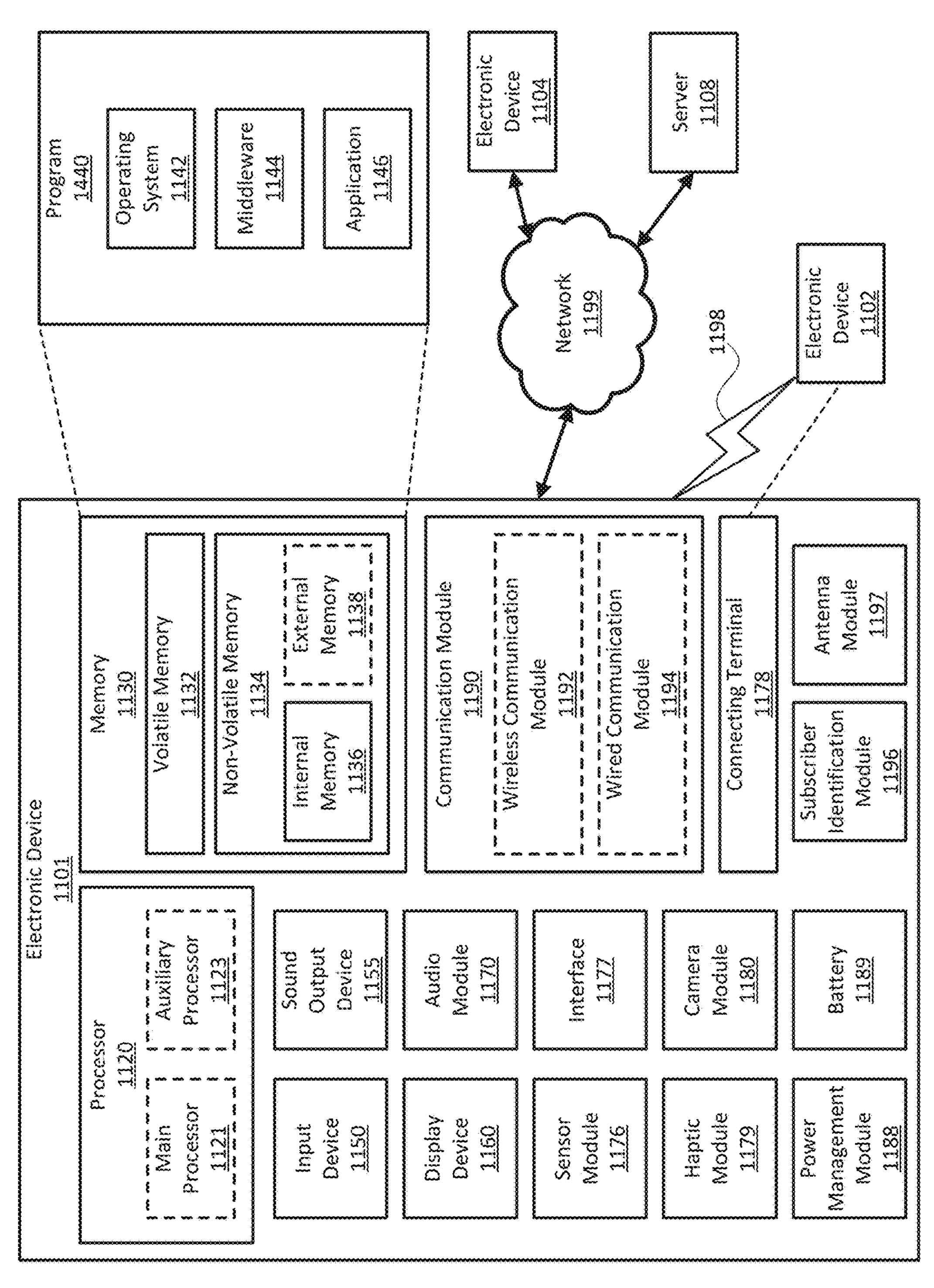
FIG. 11 is a block diagram of an electronic device in a network environment, according to an embodiment.

FIG. 11 is a block diagram of an electronic device in a network environment 1100, according to an embodiment.

Referring to FIG. 11, an electronic device 1101 (e.g., a smartwatch) in a network environment 1100 may communicate with an electronic device 1102 via a first network 1198 (e.g., a short-range wireless communication network), or an electronic device 1104 or a server 1108 via a second network 1199 (e.g., a long-range wireless communication network). The electronic device 1101 may communicate with the electronic device 1104 via the server 1108. The electronic device 1101 may include a processor 1120, a memory 1130, an input device 1150, a sound output device 1155, a display device 1160, an audio module 1170, a sensor module 1176, an interface 1177, a haptic module 1179, a camera module 1180, a power management module 1188, a battery 1189, a communication module 1190, a subscriber identification module (SIM) card 1196, or an antenna module 1197. In one embodiment, at least one (e.g., the display device 1160 or the camera module 1180) of the components may be omitted from the electronic device 1101, or one or more other components may be added to the electronic device 1101. Some of the components may be implemented as a single integrated circuit (IC). For example, the sensor module 1176 (e.g., a fingerprint sensor, an iris sensor, or an illuminance sensor) may be embedded in the display device 1160 (e.g., a display). The sensor module 1176 may include a PPG sensor, e.g., as illustrated in FIG. 1.

The processor 1120 may execute software (e.g., a program 1140) to control at least one other component (e.g., a hardware or a software component) of the electronic device 1101 coupled with the processor 1120 and may perform various data processing or computations.

As at least part of the data processing or computations, the processor 1120 may load a command or data received from another component (e.g., the sensor module 1176 or the communication module 1190) in volatile memory 1132, process the command or the data stored in the volatile memory 1132, and store resulting data in non-volatile memory 1134. The processor 1120 may include a main processor 1121 (e.g., a central processing unit (CPU) or an application processor (AP)), and an auxiliary processor 1123

(e.g., a graphics processing unit (GPU), an image signal processor (ISP), a sensor hub processor, or a communication processor (CP)) that is operable independently from, or in conjunction with, the main processor 1121. Additionally or alternatively, the auxiliary processor 1123 may be adapted to consume less power than the main processor 1121, or execute a particular function. The auxiliary processor 1123 may be implemented as being separate from, or a part of, the main processor 1121.

The auxiliary processor 1123 may control at least some of the functions or states related to at least one component (e.g., the display device 1160, the sensor module 1176, or the communication module 1190) among the components of the electronic device 1101, instead of the main processor 1121 while the main processor 1121 is in an inactive (e.g., sleep) state, or together with the main processor 1121 while the main processor 1121 is in an active state (e.g., executing an application). The auxiliary processor 1123 (e.g., an image signal processor or a communication processor) may be implemented as part of another component (e.g., the camera module 1180 or the communication module 1190) functionally related to the auxiliary processor 1123.

The memory 1130 may store various data used by at least one component (e.g., the processor 1120 or the sensor module 1176) of the electronic device 1101. The various data may include, for example, software (e.g., the program 1140) and input data or output data for a command related thereto. The memory 1130 may include the volatile memory 1132 or the non-volatile memory 1134. Non-volatile memory 1134 may include internal memory 1136 and/or external memory 1138.

The program 1140 may be stored in the memory 1130 as software, and may include, for example, an operating system (OS) 1142, middleware 1144, or an application 1146.

The input device 1150 may receive a command or data to be used by another component (e.g., the processor 1120) of the electronic device 1101, from the outside (e.g., a user) of the electronic device 1101. The input device 1150 may include, for example, a microphone, a mouse, or a keyboard.

The sound output device 1155 may output sound signals to the outside of the electronic device 1101. The sound output device 1155 may include, for example, a speaker or a receiver. The speaker may be used for general purposes, such as playing multimedia or recording, and the receiver may be used for receiving an incoming call. The receiver may be implemented as being separate from, or a part of, the speaker.

The display device 1160 may visually provide information to the outside (e.g., a user) of the electronic device 1101. The display device 1160 may include, for example, a display, a hologram device, or a projector and control circuitry to control a corresponding one of the display, hologram device, and projector. The display device 1160 may include touch circuitry adapted to detect a touch, or sensor circuitry (e.g., a pressure sensor) adapted to measure the intensity of force incurred by the touch.

The audio module 1170 may convert a sound into an electrical signal and vice versa. The audio module 1170 may obtain the sound via the input device 1150 or output the sound via the sound output device 1155 or a headphone of an external electronic device 1102 directly (e.g., wired) or wirelessly coupled with the electronic device 1101.

The sensor module 1176 may detect an operational state (e.g., power or temperature) of the electronic device 1101 or an environmental state (e.g., a state of a user) external to the electronic device 1101, and then generate an electrical signal or data value corresponding to the detected state. The sensor module 1176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1177 may support one or more specified protocols to be used for the electronic device 1101 to be coupled with the external electronic device 1102 directly (e.g., wired) or wirelessly. The interface 1177 may include, for example, a high-definition multimedia interface (HDMI), a universal serial bus (USB) interface, a secure digital (SD) card interface, or an audio interface.

A connecting terminal 1178 may include a connector via which the electronic device 1101 may be physically connected with the external electronic device 1102. The connecting terminal 1178 may include, for example, an HDMI connector, a USB connector, an SD card connector, or an audio connector (e.g., a headphone connector).

The haptic module 1179 may convert an electrical signal into a mechanical stimulus (e.g., a vibration or a movement) or an electrical stimulus which may be recognized by a user via tactile sensation or kinesthetic sensation. The haptic module 1179 may include, for example, a motor, a piezoelectric element, or an electrical stimulator.

The camera module 1180 may capture a still image or moving images. The camera module 1180 may include one or more lenses, image sensors, image signal processors, or flashes. The power management module 1188 may manage power supplied to the electronic device 1101. The power management module 1188 may be implemented as at least part of, for example, a power management integrated circuit (PMIC).

The battery 1189 may supply power to at least one component of the electronic device 1101. The battery 1189 may include, for example, a primary cell which is not rechargeable, a secondary cell which is rechargeable, or a fuel cell.

The communication module 1190 may support establishing a direct (e.g., wired) communication channel or a wireless communication channel between the electronic device 1101 and the external electronic device (e.g., the electronic device 1102, the electronic device 1104, or the server 1108) and performing communication via the established communication channel. The communication module 1190 may include one or more communication processors that are operable independently from the processor 1120 (e.g., the AP) and supports a direct (e.g., wired) communication or a wireless communication. The communication module 1190 may include a wireless communication module 1192 (e.g., a cellular communication module, a short-range wireless communication module, or a global navigation satellite system (GNSS) communication module) or a wired communication module 1194 (e.g., a local area network (LAN) communication module or a power line communication (PLC) module). A corresponding one of these communication modules may communicate with the external electronic device via the first network 1198 (e.g., a short-range communication network, such as BLUETOOTH™, wireless-fidelity (Wi-Fi) direct, or a standard of the Infrared Data Association (IrDA)) or the second network 1199 (e.g., a long-range communication network, such as a cellular network, the Internet, or a computer network (e.g., LAN or wide area network (WAN)). These various types of communication modules may be implemented as a single component (e.g., a single IC), or may be implemented as multiple components (e.g., multiple ICs) that are separate from each other. The wireless communication module 1192 may identify and authenticate the electronic device 1101 in a communication network, such as the first network 1198 or the second network 1199, using subscriber information (e.g., international mobile subscriber identity (IMSI)) stored in the subscriber identification module 1196.

The antenna module 1197 may transmit or receive a signal or power to or from the outside (e.g., the external electronic device) of the electronic device 1101. The antenna module 1197 may include one or more antennas, and, therefrom, at least one antenna appropriate for a communication scheme used in the communication network, such as the first network 1198 or the second network 1199, may be selected, for example, by the communication module 1190 (e.g., the wireless communication module 1192). The signal or the power may then be transmitted or received between the communication module 1190 and the external electronic device via the selected at least one antenna.

Commands or data may be transmitted or received between the electronic device 1101 and the external electronic device 1104 via the server 1108 coupled with the second network 1199. For example, measured PPG data may be transmitted to the external electronic device 1104, which translates the measured PPG to translated ECG, and analyzes the translated ECG, and provides information regarding the analyzed ECG, e.g., AFib detection, back to the electronic device 1101. Each of the electronic devices 1102 and 1104 may be a device of a same type as, or a different type, from the electronic device 1101. All or some of operations to be executed at the electronic device 1101 may be executed at one or more of the external electronic devices 1102, 1104, or 1108. For example, if the electronic device 1101 should perform a function or a service automatically, or in response to a request from a user or another device, the electronic device 1101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request and transfer an outcome of the performing to the electronic device 1101. The electronic device 1101 may provide the outcome, with or without further processing of the outcome, as at least part of a reply to the request. To that end, a cloud computing, distributed computing, or client-server computing technology may be used, for example.

Figure 12:
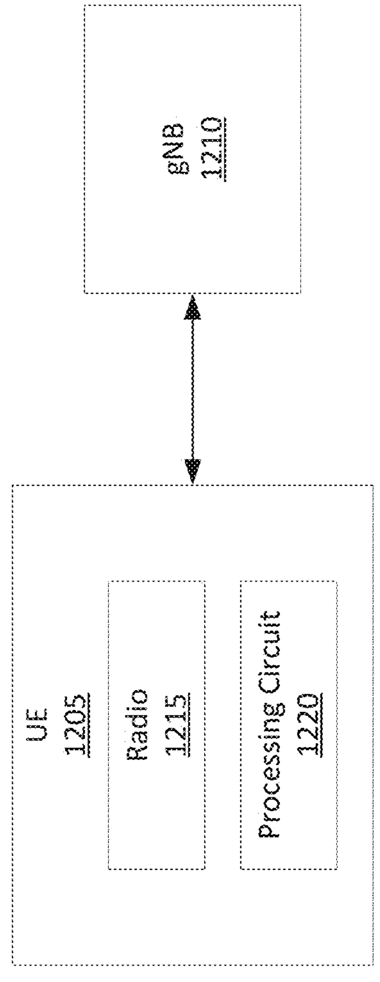
FIG. 12 shows a system including a UE and a gNB in communication with each other.

FIG. 12 shows a system including a UE 1205 and a gNB 1210, in communication with each other. The UE may include a radio 1215 and a processing circuit (or a means for processing) 1220, which may perform various methods disclosed herein, e.g., the method illustrated in FIG. 1. For example, the processing circuit 1220 may receive, via the radio 1215, transmissions from the network node (gNB) 1210, and the processing circuit 1220 may transmit, via the radio 1215, signals to the gNB 1210.

Embodiments of the subject matter and the operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer programs, i.e., one or more modules of computer-program instructions, encoded on computer-storage medium for execution by, or to control the operation of data-processing apparatus. Alternatively or additionally, the program instructions can be encoded on an artificially-generated propagated signal, e.g., a machine-generated electrical, optical, or electromagnetic signal, which is generated to encode information for transmission to suitable receiver apparatus for execution by a data processing apparatus. A computer-storage medium can be, or be included in, a computer-readable storage device, a computer-readable storage substrate, a random or serial-access memory array or device, or a combination thereof. Moreover, while a computer-storage medium is not a propagated signal, a computer-storage medium may be a source or destination of computer-program instructions encoded in an artificially-generated propagated signal. The computer-storage medium can also be, or be included in, one or more separate physical components or media (e.g., multiple CDs, disks, or other storage devices). Additionally, the operations described in this specification may be implemented as operations performed by a data-processing apparatus on data stored on one or more computer-readable storage devices or received from other sources.

While this specification may contain many specific implementation details, the implementation details should not be construed as limitations on the scope of any claimed subject matter, but rather be construed as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described herein. Other embodiments are within the scope of the following claims. In some cases, the actions set forth in the claims may be performed in a different order and still achieve desirable results. Additionally, the processes depicted in the accompanying figures do not necessarily require the particular order shown, or sequential order, to achieve desirable results. In certain implementations, multitasking and parallel processing may be advantageous.

In accordance with the above-described embodiments, an attention-based deep state-space model is provided to generate ECG waveforms with PPG signals as inputs. The model provides the ability for a paradigm shift in telemedicine by bringing about ECG-based clinical diagnoses of heart disease via simple PPG assessment through wearable devices. The model, trained on healthy subjects, achieves an average Pearson's correlation of 0.858, root mean square error (RMSE) of 0.07 mV, and SNR of 15.365 dB on a small real-world dataset, demonstrating efficacy. Significantly, the model provides AFib monitoring capability in a continuous setting, achieving a PR-AUC of 0.986. Being a lightweight model also facilitates its deployment on resource-constrained devices. Accordingly, the above-described embodiments allow for the screening and early detection of cardiovascular diseases in the home environment, which saves money and labor while supporting society in unusual pandemic situations.

As will be recognized by those skilled in the art, the innovative concepts described herein may be modified and varied over a wide range of applications. Accordingly, the scope of claimed subject matter should not be limited to any of the specific exemplary teachings discussed above, but is instead defined by the following claims.

What is claimed is:

1. A method for atrial fibrillation (AFib) detection, the method comprising:

receiving photoplethysmogram (PPG) signals of a user measured by a PPG sensor;

translating the measured PPG signals into electrocardiogram (ECG) signals using a dynamic model;

analyzing the translated ECG signals using an AFib detection model, which is trained on measured ECG signals for AFib detection, wherein analyzing the translated ECG signals comprises replacing a translated ECG signal corresponding to a time t with a measured ECG signal; and providing the analyzed AFib detection results to the user.

2. The method of claim 1, wherein analyzing the translated ECG signals using the AFib detection model further comprises:

determining that the measured ECG signal is available for the time t;

replacing the translated ECG signal corresponding to the time t with the measured ECG signal; and analyzing the measured ECG signal and the translated ECG signals, except for the translated ECG signal replaced by the measured ECG signal, using the AFib detection model.

3. The method of claim 1, wherein analyzing the translated ECG signals using the AFib detection model further comprises:

fusing the translated ECG signal at the time t with the measured ECG available for the time t, wherein the fused ECG signal at the time t is the same as the translated ECG signal, if a measured ECG is not available at the time t;

retraining the AFib detection model on the fused ECG signals; and analyzing the fused ECG signals using the retrained AFib detection model.

4. The method of claim 1, wherein generating the dynamic model comprises combining a sequential deep generative model with a state-space model augmented by an attention mechanism.

5. The method of claim 4, wherein the state-space model is generated using an ECG generative decoding process and a latent state inference posterior encoding process.

6. The method of claim 5, wherein the ECG generative decoding process includes determining ECG segments based on PPG segments and latent states.

7. The method of claim 6, wherein an ECG segment is defined by a time elapsed between two successive R peaks on an ECG signal.

8. The method of claim 6, wherein a PPG segment is defined by a time elapsed between two successive systolic peaks on a PPG signal.

9. The method of claim 5, wherein the latent state inference posterior encoding process includes determining latent states corresponding to ECG segments based on the ECG segments and recurrent states.

10. The method of claim 4, wherein the attention mechanism includes attention weights defining a quantity of each source segment to be considered for each output interval.

11. A system for atrial fibrillation (AFib) detection, the system comprising:

a photoplethysmogram (PPG) sensor; and a processor configured to:

receive PPG signals of a user measured by the PPG sensor, translate the measured PPG signals into electrocardiogram (ECG) signals using a dynamic model, analyze the translated ECG signals using an AFib detection model, which is trained on measured ECG signals for AFib detection, wherein analyzing the translated ECG signals comprises replacing a translated ECG signal corresponding to a time t with a measured ECG signal, and provide the analyzed AFib detection results to the user.

12. The system of claim 11, wherein the processor is further configured to analyze the translated ECG signals using the AFib detection model by:

determining that the measured ECG signal is available for the time t, replacing the translated ECG signal corresponding to the time t with the measured ECG signal, and analyzing the measured ECG signal and the translated ECG signals, except for the translated ECG signal replaced by the measured ECG signal, using the AFib detection model.

13. The system of claim 11, wherein the processor is further configured to analyze the translated ECG signals using the AFib detection model by:

fusing the translated ECG signal at the time t with the measured ECG available for the time t, wherein the fused ECG signal at the time t is the same as the translated ECG signal, if a measured ECG is not available at the time t;

retraining the AFib detection model on the fused ECG signals, and analyzing the fused ECG signals using the retrained AFib detection model.

14. The system of claim 11, wherein the processor is further configured to generate the dynamic model by combining a sequential deep generative model with a state-space model augmented by an attention mechanism.

15. The system of claim 14, wherein the processor is further configured to generate the state-space model using an ECG generative decoding process and a latent state inference posterior encoding process.

16. The system of claim 15, wherein the ECG generative decoding process includes determining ECG segments based on PPG segments and latent states.

17. The system of claim 16, wherein an ECG segment is defined by a time elapsed between two successive R peaks on an ECG signal.

18. The system of claim 16, wherein a PPG segment is defined by a time elapsed between two successive systolic peaks on a PPG signal.

19. The system of claim 15, wherein the latent state inference posterior encoding process includes determining latent states corresponding to ECG segments based on the ECG segments and recurrent states.

20. The system of claim 14, wherein the attention mechanism includes attention weights defining a quantity of each source segment to be considered for each output interval.

* * * * *